United States Patent [19]

Howard, Jr.

[11] Patent Number: 4,786,555

[45] Date of Patent: Nov. 22, 1988

[54] SUPPORT PARTICLES COATED WITH OR PARTICLES OF PRECURSORS FOR OR OF BIOLOGICALLY ACTIVE GLASS

[75] Inventor: Edward G. Howard, Jr., Hockessin, Del.

[73] Assignee: E. I. Du Pont de Nemours and Company, Wilmington, Del.

[21] Appl. No.: 871,886

[22] Filed: Jun. 9, 1986

Related U.S. Application Data

[62] Division of Ser. No. 546,152, Oct. 27, 1983, Pat. No. 4,608,350.

[51] Int. Cl.$^4$ .......................... B32B 5/16; A61F 2/02; A61F 2/28
[52] U.S. Cl. ..................................... 428/403; 428/404; 428/406; 623/16; 623/11
[58] Field of Search ....................... 428/403, 404, 406; 501/11, 27, 29, 30, 33, 55, 56, 57, 58, 63, 65; 623/11, 16, 16 D, 16 G

[56] References Cited

U.S. PATENT DOCUMENTS

| | | | |
|---|---|---|---|
| 3,811,918 | 5/1974 | Levene | 501/27 X |
| 4,063,916 | 12/1977 | De Vos et al. | 501/65 X |
| 4,103,002 | 7/1978 | Hench et al. | 428/155 |
| 4,135,935 | 1/1979 | Pfeil et al. | 106/35 |
| 4,159,358 | 6/1979 | Hench et al. | 427/318 |
| 4,171,544 | 10/1979 | Hench et al. | 3/1.9 |
| 4,220,461 | 9/1980 | Samanta | 65/22 |

FOREIGN PATENT DOCUMENTS

1282307 7/1972 United Kingdom.

OTHER PUBLICATIONS

Hench, "Biomaterials", *Science*, 208, 826 to 831 (1980).
Hall, *J. Biomed. Mater. Res. Symposium*, No. 2 (Part 1), pp. 1 to 4 (1971).

*Primary Examiner*—John E. Kittle
*Assistant Examiner*—Susan S. Rucker
*Attorney, Agent, or Firm*—James A. Costello

[57] ABSTRACT

An aqueous solution of precursors for biologically active glass, support particles coated with the solution, support particles coated with the glass, spheroidal particles of biologically active glass, processes for making the solution, coating the support, and for making the coated support and the spheroidal glass particles. The materials that comprise the biologically active glass are useful in prosthetic devices and implants for the human body.

6 Claims, No Drawings

SUPPORT PARTICLES COATED WITH OR PARTICLES OF PRECURSORS FOR OR OF BIOLOGICALLY ACTIVE GLASS

CROSS-REFERENCE TO RELATED APPLICATION

This is a division of application bearing U.S. Ser. No. 546,152 filed on Oct. 27, 1983 now U.S. Pat. No. 4,608,350 issued Aug. 26, 1986.

BACKGROUND OF THE INVENTION

This invention concerns precursors for biologically active glass in the form of a stable aqueous solution, spheroidal glass particles, supports coated with the precursors, supports coated with the glass, and methods for making the precursor solution, the coated support and the glass particles.

As pointed out by Hench in a review article entitled "Biomaterials" in *Science*, 208, 826 to 831 (1980), some 2 to 3 million artificial or prosthetic parts are implanted in individuals in the United States each year. These devices, made from a wide variety of materials, are useful, for example, in the eye, the ear, and the nervous system; in the heart, limbs, bladder, and blood vessels; and to repair and replace bones, ligaments, and teeth. In these uses they combat both the degenerative effects of aging and damage resulting from accidents.

A summary of the status of biomaterials and the problems associated with them has been presented by Hall in *J. Biomed. Mater. Res. Symposium*, No. 2 (Part 1), pages 1 to 4 (1971). The article stresses the importance of the interface between an implant and the body tissue of the host.

U.S. Pat. No. 4,171,544 discloses numerous biologically active glass compositions.

U.S. Pat. No. 4,103,002 discloses a method for coating an alumina, ceramic surface with a biologically active glass. The patent points out that alumina ceramic surfaces are biologically inactive and that bone tissue will not bond to or grow on them.

U.S. Pat. No. 4,159,358 discloses a method for bonding a biologically active glass to a metal surface. In discussing the use of biologically active glasses as biomaterials, the patent states that it is impossible to construct sufficiently strong orthopedic or dental devices from them.

U.S. Pat. No. 4,220,461 discloses deposition of a porous body by the combination of two separate solutions, one a,cidic and one basic, of glass precursors. U.S. Pat. No. 4,135,935 discloses a composite material of biologically active glass and a mineral apatite. GB No. 1,282,307 discloses a method for preparing oxides of two or more elements employing a highly complexing organic substance which is decomposed upon heating.

SUMMARY OF THE INVENTION

This invention concerns an aqueous acid solution composition of precursors for biologically active glass. The aqueous acid solution of the invention comprises a combination of all the precursors necessary to give a finished product when the precursor composition is dried and fired. This invention is not limited to any particular precursors for any specific biologically active glass. On the contrary, any combination of precursors can be employed which will form a coating of biologically active glass on the support particles.

The term "biologically active glass" means that the glass can form in vivo bonds with bone, muscle and other body tissues. For the sake of brevity, the term "glass" is employed herein to refer to biologically active glass. The term "aqueous solution" means an aqueous acid solution, suspension or dispersion of glass precursors.

This invention also concerns compositions of support particles coated with the glass precursors and support particles coated with the glass formed by calcining the glass precursors. This invention also concerns spheroidal particles of biologically active glass made by spray-drying the glass precursors and firing the spray-dried particles. Also included within the scope of this invention are methods for making the solution compositions of glass precursors, for coating the support particles, for drying and firing the precursor-coated supports to form glass-coated/fused support particles and for spray-drying the solution compositio of glass precursors. The spheroidal particles are characterized by their generally spheroidal geometry and relatively smooth surfaces. Glass particles of this invention can be easily distinguished from the rough-edged, substantially hon-spherical glass particles of the prior art by microscopic examination.

DETAILS OF THE INVENTION

The Biologically Active Glass

The following patents disclose a number of biologically active glasses that can be made by the process of this invention: U.S. Pat. Nos. 4,159,358, 4,103,002 and 4,171,544. In general, this invention encompasses any glass whose components can be prepared in a stable aqueous solution. By "stable" is meant that there is no substantial amount of precipitation in a period of one hour.

A typical composition range for a subclass of contemplated glass, which according to the convention used in glass chemistry is given in terms of oxides and fluoride, is as follows:

| Component | Weight Percent |
|---|---|
| $SiO_2$ | 40 to 62 |
| $Na_2O$ | 10 to 32 |
| $CaO$ | 10 to 32 |
| $CaF_2$ | 0 to 18 |
| $P_2O_5$ | 0.1 to 12 |
| $B_2O_3$ | 0 to 20, | wherein the sum of $Na_2O$ and $CaO$ is at least about 30 weight percent. Of the listed components, $CaF_2$ is not water-soluble. Consequently, an aqueous solution of glass precursors that comprises $CaF_2$ as a component is treated to suspend the $CaF_2$. One method of treatment comprises adding a solution of fluoride ions (via NaF or $NH_4F$) to a solution of $Ca^{++}$ with vigorous mixing. Preferred glasses of this type contain about 0.5 to 6 weight percent of $P_2O_5$.

Another subclass of contemplated glasses comprises those that contain boron. A typical boron-containing glass contains: 40 wt percent of $SiO_2$, 5 wt percent of $B_2O_3$, 6 wt percent of $P_2O_5$, 24.5 wt percent of $CaO$, and 24.5 wt percent of $Na_2O$.

The Support

Contemplated materials that can be employed as supports for the glass include high melting mineral oxides, ceramics, and the like. In fact, any material can be employed that will not adversely react with the glass, glass precursors or body parts with which said material may come in contact. It will be understood, of course, that said material should be relatively tough and stable at the elevated temperatures employed to fire the glass.

Contemplated support materials include alumina, silica, carbon, silica-aluminas, titania, clays, calcium silicate, feldspar, zinc oxide and the like, including any metal that the body will accept. The support can be selected from at least one member of the group alumina, silica, titania, clay, calcium silicate, feldspar, zinc oxide and mixtures and compositions containing at least one of the members. Preferred supports are alumina, silica, titania, and mixtures and compositions thereof. The iize and concentration of the support particles will vary in accordance with the particular device being fabricated, its intended use, and the desire,d composition of the particles. Contemplated particle sizes range up to about 1 mm or more in diameter.

A sodium and silica-containing compound such as $Na_2O.(SiO_2)_{3.38}$ or $Na_2SiO_3$ or $(NaO)_2Si(CH_3)_2$ can be usd as a precursor for $SiO_2$ and $Na_2O$. Other precursors for $SiO_2$ include silicic acid and colloidal $SiO_2$. The precursors for CaO include the calcium salt of a $C_1$ to $C_4$ alkanoic acid, preferably calcium formate, $Ca(O_2CH)_2$, and, when $HNO_3$ is used to control pH, $Ca(NO_3)_2$. Precursors for $P_2O_5$ and $Na_2O$, are the sodium phosphates, $Na_3PO_4$, $Na_2HPO_4$, $NaH_2PO_4$, $Na_2H_2P_2O_7$ and the sodium phosphites $Na_3PO_3$, $Na_2HPO_3$ and $NaH_2PO_3$. Preferred is the sodium phosphate $Na_3PO_4.12H_2O$. Other precursors for $P_2O_5$ include $H_3PO_4$ and the ammonium salts equivalent to the above sodium salts. The precursors for $B_2O_3$ include the sodium borates, which also provide $Na_2O$. Preferred is $Na_2B_4O_7.10H_2O$. Precursors for $Na_2O$ include the sodium salts mentioned above as well as the sodium salt of a $C_1$ to $C_4$ alkanoic acid, preferably sodium formate, and, when $HNO_3$ is used to control pH, $NaNO_3$. The introduction of ions such as $SO_4^{-2}$ and $Al^{+3}$ that would immediately form precipitates with other ions present should be avoided. Other ions that enhance biological growth can also be introduced into the solution. These ions include $Mg^{+2}$; see Jaffe "Metabolic Degenerative and Inflammatory Diseases of Bones and Joints", Lea and Febiger, Phila. (1972) page 124 and following. Should $K_2O$ be desired as a component of the glass, it can be included in the precursor solution as $KHCO_3$, $KNO_3$ or $KOC(O)R$.

The aqueous solution compositions of this invention have a pH typically below about 5. Preferred acids for pH control are whose which decompose cleanly on heating and leave no carbon residue that would require prolonged ignition. Such clean deposition is a general requirement for an acid whose are used or which is used in the free state. Enough acid is added to the solution to achieve the desired pH. Acids that meet the requirements of relatively high volatility and clean decomposition include nitric acid and $C_1$ to $C_4$ alkanoic acids, includng any acid whose calcium and sodium salts are used in making up the solution or dispersion. Since these salts are preferably formates, the most preferred acid is formic acid. For formic acid and nitric acids the pH will be at most about 3.8, and preferably about 3.3 to 3.8. For acetic acid, propionic acid, and the butyric acids the pH will be at most about 4.6, and preferably about 4.1 to 4.6. The optimum pH for any particular glass precursor composition can readily be determined by simple experiment.

In the actual coating operation, the particulate support to be coated is intimately mixed with a freshly prepared solution of glass precursors with agitation and preferably with gentle grinding. In the laboratory, mixing, agitation, and grinding are conveniently accomplished with a mortar and pestle. The wet solid can then be air-dried to remove all or part of the water; spray-drying techniques being preferred. The dried solid is then heated at a temperature high enough to remove any remaining water, volatilize and/or decompose any remaining formic acid, and convert the component of the coating medium to the desired glass. This temperature is usually about 600° C. to 1550° C. although somewhat lower temperatures can sometimes be employed effectively.

A convenient method for making up the coating solution to minimize the chance of precipitation is to make up two solutions, the first containing calcium formate and sodium formate, if any, and the second containing sodium silicate and whatever sodium phosphate and/or sodium borate is to be used. Formic acid is then dissolved in either solution, and the two solutions are mixed rapidly with good agitation. The amount of formic acid to be used can be easily determined by simple experiments with aliquots of the two solutions.

The relative amount of each inorganic precursor dissolved in the coating medium will be equivalent to the relative amount of the corresponding inorganic component necessary to form the desired glass. Usually, the concentration of precursors will be about 100 g to 200 g per liter of solution. A lower concentrations, an unnecessarily large amount of water has to be evaporated in the heating step; at higher concentrations there is a greater tendency to form precipitates. The support particles contacted with said precursors will vary in size and concentration according to the weight and/or volume relationship desired in the glass-coated support product. Multiple coating/drying/sintering steps can also be employed.

The biologically active glasses that are made by the precursor solution process of this invention are well accepted as components in biomedical products including devices, prostheses, replacement parts and implants for the body. The utility of the supported biologically active glass of this invention is at least coextensive with that of unsupported biologically active glass. In addition, the supported glass has strength/smoothness/rigidity and density advantages—balanced with homogeneous composition characteristics—not heretofore possible.

Coated supports can be sintered and/or fused onto nearly any compatible substrate to form large or small devices of almost any geometry. The coated supports can also be molded or cast to form biomedical devices comprised solely of the support and glass described herein in a uniform, homogeneous and body-compatible matrix.

The requirements met by biomedical materials made from the supported glass of this invention are as follows: (1) their properties approximate those of the body part that they replace or in which they are incorporated; (2) they are accepted by the living host without adverse reactions such as inflammation or toxicity; (3) they form in vivo bonds with host tissues; and (4) their implantation does not cause the formation of more than a relatively thin "capsule" at their interface with the host's body part.

EXAMPLE 1

Two solutions were made up as follows: Solution I contained 56.9 g of calcium formate, 6.1 g of sodium formate, and enough water to make 500 ml of solution; its pH was 6.6. Solution II contained 32.0 g of $Na_3PO_4.12H_2O$, 158.5 g of $Na_2O.(SiO_2)_{3.38}$ as an aqueous 37.1% solution, and enough water to make 500 ml of solution; its pH was 10.9.

To 37.5 ml of solution I was added 5.3 ml of formic acid, and the resulting solution was added rapidly with good stirring to 37.5 ml of solution II. The combined solution was added slowly to 155 g of alumina in a mortar as the mixture was stirred with a pestle. The alumina was obtained by calcining $Al_2O_3.3H_2O$ (Alcoa C30BF). Stirring was continued until the mixture was uniform. The product was fired at 1200° C. in a muffle furnace overnight. The solid was again surface-treated by the method described in this paragraph, to give a biologically active glass-coated alumina that had a surface area of 35.6 $m^2/g$. The product contained 48.1% of Al, corresponding to an overall glass/alumina composition of about 9/91.

EXAMPLE 2

Alumina was coated with biologically active glass by substantially the method of Example 1, with the following changes: The alumina was calcined "Alcoa" C333B $Al_2O_3.3H_2O$; the quantities were 600 g of alumina, 180 ml of solution I, 180 mL of solution II, and 25.2 ml of formic acid; after mixing with the liquid, the treated alumina was air-dried overnight and then fired at 1200° C. for one hour.

Loose aggregates were broken up in a blender cup to give a particulate glass-coated alumina that had a surface area of 7.4 $m^2/g$. A representative sample was fractionated sequentially through sieves of increasing fineness and showed the following particle size distribution: on 80-mesh screen 2%; through 80, on 200, 13%; through 200, on 325, 45%; and through 325, 35%.

EXAMPLE 3

An aqueous solution of a biologically active glass having the following composition was made without formation of a precipitate: 40% $SiO_2$, 5% $B_2O_3$, 6% $P_2O_5$, 24.5% CaO, and 24.5% $Na_2O$. The two precursor solutions contained the following reagents.

Solution I 2.4 g $NaO_2CH$
56.9 g $Ca(O_2CH)_2$
Final volume: 600 ml (water).

Solution II 140.7 g 37.1% solution $Na_2O.3.38\ SiO_2$
13.6 g $Na_2B_4O_7.10H_2O$
32.1 g $Na_3PO_4.12\ H_2O$
Final volume: 600 ml (water).

The mixing of Solutions I and II was accomplished as follows. Formic acid (0.5 ml) was added with 5 ml of water to Solution II. Then 5 ml of I was added fast with agitation. This gave a clear solution that did not gel until after 3 days at room temperature.

The powdered alumina was coated as follows: first, Alcoa C-331 $Al_2O_3.3\ H_2O$ (gibbsite) having a size classification of
  94 to 99% less than 30 microns,
  85 to 93% less than 20 microns,
  56 to 67% less than 10 microns, and
  20 to 40% less than 5 microns,
was calcined at 400° C.

The alumina (100 g) was then ground with a solution of the biologically active glass made from 25 ml of Solution I, 3 ml of formic acid, and 25 ml of Solution II. The wet solid was air dried, then fired in a platinum dish at 1200° C. for 30 min to give 102 g of free flowing solid. This powder (75 g) was retreated using 15 ml of Solution I, 1.8 ml of formic acid, and 15 ml of Solution II. The final product was a white powder (80 g). This powder in water raises the pH to about 10.

EXAMPLE 4

Two solutions were prepared as follows:
(I) 237.6 g of calcium formate, 114.4 g of sodium formate, and enough distilled water to give 4 liters of solution.
(II) 158.4 g of $Na_4P_2O_7.10H_2O$, 1,448.8 g of 7.1% $Na_2O.3.38\ SiO_2$, and enough water to give 4 liters of solution.

To 720 ml of Solution I containing 160 ml of formic acid in a blender cup was added with vigorous stirring 720 ml of Solution II. This final solution was spray-dried to a fine white powder.

The powder contained water and formates that were removed as follows. To a 1 liter 3-necked flask fitted with a paddle stirrer, thermocouple, and slow nitrogen purge was added 25 g of the powder with heating and stirring. The particles gassed vigorously at 350° to 400°. More powder was added using hot powder as a diluent. As drying progressed, powder was added more quickly. The final product (214 g from 409.6 g of spray-dried powder) was heated at 800° C. in a muffle furnace and then ground to a powder. When further heated to 920° C. the dark gray product was a porous, easily crushed glass foam of composition corresponding to the 53.0% $SiO_2$, 12.8% CaO, 23.0% NaO and 6.3% $P_2O_5$ of U.S. Pat. No. 4,171,544.

EXAMPLE 5

This Example was carried out in a manner similar to that of Example 4.

Solution I 2.4 g of sodium formate,
56.9 g of calcium formate,
enough water to give 600 ml.

Solution II 140.7 g of 37.1% $Na_2O.3.38\ SiO_2$ in water,
13.6 g of $Na_2B_4O_7.10H_2O$,
32.1 g of $Na_3PO_4.12H_2O$,
enough water to give 600 ml.

To prepare the solution for spray drying, 720 ml of Solution I and 100.8 ml of formic acid were put in a blender cup and stirred vigorously while adding 720 ml of Solution II. The solution was then spray dried and heated and stirred as described in Example 4. After the heat was raised to 1050° C., the resulting product was a friable white solid easily crushed in a mortar and pestle to a white powder. Based on the amounts of material used, this product had this composition by weight:

$Na_2O$, 23.7%; CaO, 24.8%; $P_2O_5$, 6.0%; $SiO_2$, 40.5%; and $B_2O_3$, 5.0%.

EXAMPLE 6

Calcined $Al_2O_3.3H_2O$ (Alcoa C30BF) was coated with glass. Particle size distribution was as follows:
80 to 85% pass through a #325 sieve, i.e., are less than 45 μm, and
97 to 99% pass through a #200 sieve, i.e., are less than 75 μm.

Two solutions were made up as follows: Solution I contained 56.9 g of calcium formate, 6.1 g of sodium formate, and enough water to make 500 ml of solution; its pH was 6.6. Solution II contained 32.0 g of $Na_3PO_4$ $12H_2O$, 158.5 g of $Na_2O.(SiO_2)_{3.38}$ as an aqueous 37.1% solution, and enough water to make 500 ml of solution; its pH was 10.9.

To 50 ml of Solution I was added 7 ml of formic acid, and the resulting solution was added rapidly with good stirring to 50 ml of Solution II. The combined solution was added slowly to 200 g of alumina in a mortar as the mixture was stirred with a pestle. Stirring was continued until the mixture was uniform. The product was fired at 1200° C. in a muffle furnace overnight. The solid was again surface-treated by the method described in this paragraph, to give a glass-coated alumina.

EXAMPLE 7

Spray-dried biologically active glass powder was made from: Solution I—68.3 g of calcium formate—7.3 g of sodium formate—enough water to give 600 ml of solution. Solution II—190.2 g of 37.1% $Na_2O$, 3.38 g of $SiO_2$—38.5 g of $Na_3PO_4.12H_2O$ and enough water to give 600 ml of solution. Additional solutions were prepared until 4 liters of each had been made.

To 720 ml of Solution I and 100 ml of formic acid in a blender cup was added 720 ml of Solution II with vigorous stirring. This final solution was then spray-dried.

A 3 necked round bottom flask was fitted with a paddle stirrer and a $N_2$ inlet tube, and was heated with a Meeker burner. About 25 g of the spray-dried powder was placed in the nitrogen-purged flask, the stirrer was started and the burner was turned on. The powder stuck together as liquids began to distill from the flask. On continued heating, the particles became free flowing and at 380° C., they degassed vigorously liberating a flammable gas, probably CO and $H_2$. More spray-dried material was added at such a rate that agglomeration did not occur. Over 35 min, 320 g of spray-dried material was added. The stirred solid was heated to 520° C. and cooled. The experiment required 45 min and gave 210 g of brown free-flowing powder. When heated to 950° C. in air, the product became a white friable cake that was easily crushed to powder with mortar and pestle.

EXAMPLE 8

This Example represents a single solution method for making biologically active glass and/or glass-coated support particles. In 15 ml of $H_2O$ was dissolved 1.6 g of $Na_3PO_4.12H_2O$. To that solution was added 7.9 g of a 37.1% aqueous solution of $Na_2O.3.38SiO_2$. Water was added to 25 ml and 5 ml of formic acid was added to give a clear solution. Then, 2.8 g of $Ca(O_2CH)_2$ and 0.3 g of $NaO_2CH$ was added with vigorous stirring. The foregoing clear solution did not gel in 1 hour. When dried and fired, this precursor solution would give a biologically active glass having the composition:
$SiO_2$—45%
$Na_2O$—24.5%
CaO—24.5%
$P_2O_5$—6%.

The precursor solution can be spray-dried and subsequently fired to form spheroidal biologically active glass particles. Alternatively, support particles of alumina, silica, carbon, silica-alumina minerals, titania, clay, calcium silicate, feldspar and zinc oxide, individually or in any combination, can be added to the solution with good agitation. Subsequent drying will produce glass precursor-coated support particles that can be dry-molded and calcined to form shaped biomedical devices. In another alternative, the glass precursor-coated support particles can be treated with an adherent including one or more individual components of biologically active glass and the adhered mass can be molded and fired.

EXAMPLE 9

This Example demonstrates generally how one can incorporate certain additives into a solution of precursors for biologically active glass. For instance, Sr, Ba, Li, Al, Fe and/or Ti components can be incorporated into an already prepared aqueous nitric acid solution of precursors. Alternatively, the glass precursors and additive precursors can be formulated in one step into a modified solution of precursors for biologically active glass. The additive components will be present in the nitric acid solution in the form of their nitrates, e.g., as $Sr(NO_3)_3$, $Ba(NO_3)_2$, $LiNO_3$, $Al(NO_3)_3$, $Fe(NO_3)_3$ or as titanyl $TiO=$ ion, respectively. Care should be taken not to mix formic acid/formates with nitric acid/nitrates because of the potential explosive hazard.

EXAMPLE 10

Cylindrical α-alumina pellets of ½ in. (1.27 cm) in diameter and ½ in. (1.27 cm) height were washed, dried, and treated with the combined aqueous solution of Example 1, air dried, and fired at 1200° C. The coating, drying, and firing procedures were repeated once and the surfaces were examined using scanning electron microscopy. The fine holes and cracks of the original alumina surface were filled. The surface was smooth and uncrazed.

The embodiments of the invention in which an exclusive property or privilege is claimed are defined as follows:

1. A method for making particles of biologically active glass comprising spray-drying an aqueous acid solution showing no substantial amount of precipitation in one hour consisting essentially of precursors that correspond to components of the glass and firing the spray-dried particles to convert the glass precursors to glass, the glass consisting essentially of the components:
$SiO_2$, 40 to 62 weight percent;
$Na_2O$, 10 to 32 weight percent;
CaO, 10 to 32 weight percent;
$CaF_2$, 0 to 18 weight percent;
$P_2O_5$, 0.1 to 12 weight percent; and
$B_2O_3$, 0 to 20 weight percent;
wherein $Na_2O$ and CaO taken together, are at least about 30 weight percent.

2. Biologically active glass particles made by the method of claim 1.

3. A spheroidal particle of biologically active glass made by the method of claim 1.

4. A biomedical device comprising a uniform, homogeneous, body-compatible matrix of particles according to claim 2.

5. A biomedical device comprising a uniform, homogeneous, body-compatible matrix of particles according to claim 3.

6. A spray-dried particle made from an aqueous acid solution showing no substantial amount of precipitation in one hour consisting essentially of biologically active glass precursors that correspond to components of a biologically active glass, the glass consisting essentially of the components:

$SiO_2$, 40 to 62 weight percent;
$Na_2O$, 10 to 32 weight percent;
$CaO$, 10 to 32 weight percent;
$CaF_2$, 0 to 18 weight percent;
$P_2O_5$, 0.1 to 12 weight percent; and
$B_2O_3$, 0 to 20 weight percent;

wherein $Na_2O$ and $CaO$ taken together, are at least about 30 weight percent.

* * * * *